US009970915B2

(12) United States Patent
Miller et al.

(10) Patent No.: US 9,970,915 B2
(45) Date of Patent: May 15, 2018

(54) SYSTEMS AND METHODS FOR RAPID MEASUREMENT OF CARBON DIOXIDE IN WATER

(71) Applicant: Smithsonian Environmental Research Center, Edgewater, MD (US)

(72) Inventors: Alexander Whitman Miller, Annapolis, MD (US); Gerhardt F. Riedel, Saint Leonards, MD (US); Karl John Klug, West Hollywood, CA (US)

(73) Assignee: Smithsonian Institution, Washington, DC (US)

( * ) Notice: Subject to any disclaimer, the term of this patent is extended or adjusted under 35 U.S.C. 154(b) by 161 days.

(21) Appl. No.: 14/937,331

(22) Filed: Nov. 10, 2015

(65) Prior Publication Data
US 2016/0061796 A1 Mar. 3, 2016

Related U.S. Application Data

(63) Continuation of application No. PCT/US2014/037738, filed on May 12, 2014.
(Continued)

(51) Int. Cl.
*G01N 33/00* (2006.01)
*G01N 33/18* (2006.01)
(Continued)

(52) U.S. Cl.
CPC .............. *G01N 33/004* (2013.01); *G01N 7/00* (2013.01); *G01N 21/3504* (2013.01);
(Continued)

(58) Field of Classification Search
CPC .... G01N 33/004; G01N 33/1886; G01N 7/00; G01N 1/10; G01N 1/2273; G01N 2201/0221; G01N 21/3504
USPC .................................. 73/19.01, 19.1; 422/50
See application file for complete search history.

(56) References Cited

U.S. PATENT DOCUMENTS 5,833,841 A 11/1998 Koslowsky
6,258,280 B1 7/2001 Petrich
(Continued)

OTHER PUBLICATIONS

Takahashi, T., Sweeney, C., Sutherland, S.C., Chipman, D.W., Goddard, J., Rubin, S.I., 2000. Method of Underway pCO2 Measurements in Surface Waters and the Atmosphere During the Aesops Expeditions, 1996-1998 in the Pacific Sector of the Southern Ocean and the Ross Sea. US JGOFS Data Center, Woods Hole Oceanographic Institution, Woods Hole, MA.*
(Continued)

*Primary Examiner* — Peter Macchiarolo
*Assistant Examiner* — Irving A Campbell
(74) *Attorney, Agent, or Firm* — Perkins Coie LLP

(57) ABSTRACT

Systems and methods are provided for rapidly determining the partial pressure of $CO_2$ ($pCO_2$) in a body of water. The systems and methods are particularly useful for measuring $pCO_2$ in coastal waters and other bodies of water where $pCO_2$ can change rapidly and vary widely at sites that are in close proximity to each other. Additionally, $pCO_2$ measurements can be important for industrial $CO_2$ sequestration monitoring, monitoring $pCO_2$ in wastewater and drinking water treatment plants, as well as monitoring and controlling pH in municipal and private swimming pools.

20 Claims, 4 Drawing Sheets

Related U.S. Application Data

(60) Provisional application No. 61/822,287, filed on May 10, 2013.

(51) Int. Cl.
 *G01N 21/3504* (2014.01)
 *G01N 7/00* (2006.01)
 *G01N 1/10* (2006.01)
 *G01N 1/22* (2006.01)

(52) U.S. Cl.
 CPC ............ *G01N 33/1886* (2013.01); *G01N 1/10* (2013.01); *G01N 1/2273* (2013.01); *G01N 2201/0221* (2013.01)

(56) References Cited

U.S. PATENT DOCUMENTS 6,536,272 B1 3/2003 Houston et al.
8,168,121 B2 5/2012 Elkins
2010/0070201 A1 3/2010 Bell et al.
2010/0206788 A1 8/2010 Von Broembsen et al.

OTHER PUBLICATIONS

Non-Patent Literature "Valco Instruments Co. Inc. Standard Multiposition Electric Valve Actuators", archived on Mar. 12, 2006, accessed at http://web.archive.org/web/20060312100701/http://www.vici.com/act/elecmp.php.*
Pierrot, D., et al. (2009), Recommendations for autonomous underway pCO2 measuring systems and data reduction routines, Deep Sea Res., Part II, 56, 512-522.*
Kortzinger, A., et al. (1997), Strong CO2 emissions from the Arabian Sea during South West Monsoon, Geophysical Research Letters, vol. 24, No. 14, pp. 1763-1766.*
Non-Patent Literature "LI-6262 CO2/H2O Analyzer", published Mar. 1996.*
International Search Report and Written Opinion for International Application No. PCT/2014/033738 dated Sep. 11, 2014.

* cited by examiner

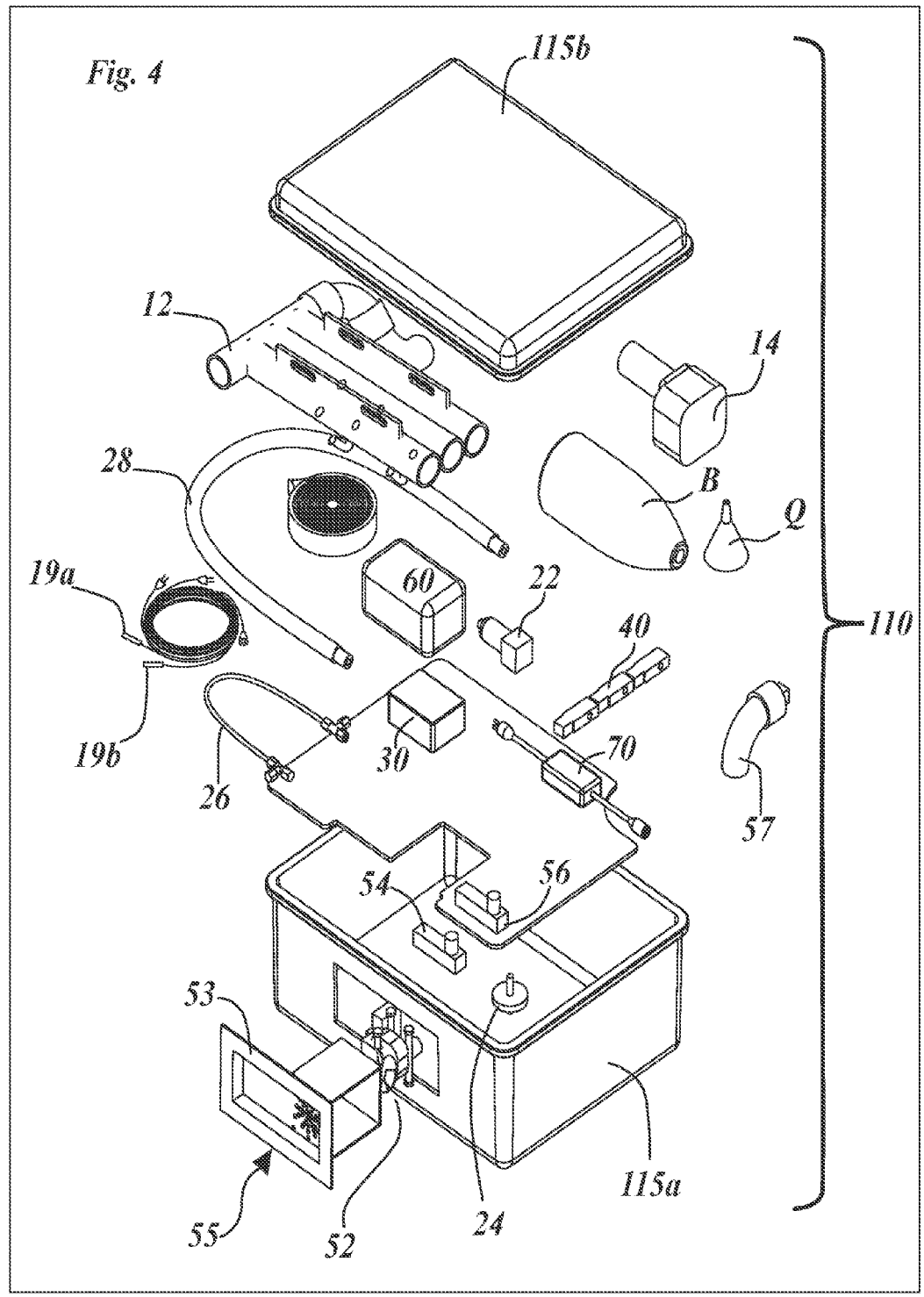

SYSTEMS AND METHODS FOR RAPID MEASUREMENT OF CARBON DIOXIDE IN WATER

This application is a continuation of International Application No. PCT/US14/37738, filed May 12, 2014, which claims the benefit of U.S. Provisional Application No. 61/822,287, filed May 10, 2013, each entitled "Systems and methods for rapid measurement of carbon dioxide in water," and the contents of each of which are hereby incorporated by reference in their entireties.

This application claims the benefit of U.S. Provisional Application No. 61/822,287, filed May 10, 2013, entitled "Systems and methods for rapid measurement of carbon dioxide in water," the contents of which are hereby incorporated by reference in their entirety.

TECHNICAL FIELD

Systems and methods for determining the concentration of a component in water are provided. More specifically, systems and methods are provided for rapidly determining the partial pressure of $CO_2$ ($pCO_2$) in a body of water. The systems and methods are particularly useful for measuring $pCO_2$ in coastal waters and other bodies of water where $pCO_2$ can change rapidly and vary widely at sites that are in close proximity to each other.

BACKGROUND

Atmospheric carbon dioxide ($CO_2$) is increasing and having an important effect on the regulation of the earth's temperature. Furthermore, roughly 30% of anthropogenic $CO_2$ leaves the atmosphere and enters the earth's oceans and other large bodies of water. These water bodies typically act as large sinks of $CO_2$, via dissolution of $CO_2$ as carbonic acid, with concomitant changes in ocean pH. Unfortunately, devices for directly measuring pH in the natural environment are unreliable when deployed for any length of time. In coastal systems where changes in salinity are common and biofouling extensive, measuring pH can burdensome. Alternatively, measurements of changes in the partial pressure of $CO_2$ in the ocean can provide valuable and reliable information about changes in the acidity of the ocean. Nearshore coastal water pH measurements can also be made providing similar information.

Methods for measuring $pCO_2$ in oceans have mainly focused on measuring acidification in open ocean settings. These methods assume that acidification is driven by a stable air-sea $CO_2$ equilibrium, such that measurement of the ocean's $pCO_2$ is reflective of atmospheric $pCO_2$. The technology depends on large, expensive, and sparse autonomous buoys to characterize hundreds to thousands of $km^2$ of ocean surrounding them. Buoy data are supplemented by data from large, expensive, and sparse oceanographic research vessel transits.

Due to the complexity of nearshore coastal waters, an air-sea equilibrium rarely occurs and measurements must be made at much higher frequencies over space and time. Increased frequencies can assist to reliably characterize $pCO_2$ and pH. In nearshore waters the carbon cycle is much more complicated than the open ocean, and land-sea interactions are frequently more acute than air-sea interactions. Nearshore waters are further complicated by biological activities such as photosynthesis and respiration and the $pCO_2$ of water is far more dynamic than in the open ocean. Changes in $pCO_2$ are more rapid than in open ocean waters and $pCO_2$ can vary significantly over very short distances and time spans. Measurements must therefore be made much more frequently and much more densely in order to capture the natural temporal and spatial variability present. Thus, use of cheaper, more numerous, portable, and easily deployable $pCO_2$ instruments is desirable.

BRIEF DESCRIPTION OF THE DRAWINGS

The accompanying drawings, which are incorporated herein and constitute part of this specification, illustrate exemplary embodiments of the systems, and together, with the general description given above and the detailed description given below, serve to explain the features of the systems. It should be understood that the preferred embodiments are some examples of the invention as provided by the appended claims and are not limiting of those claims.

FIG. 4 is an exploded view of the preferred embodiment of FIG. 3.

DETAILED DESCRIPTION

Figure 1:
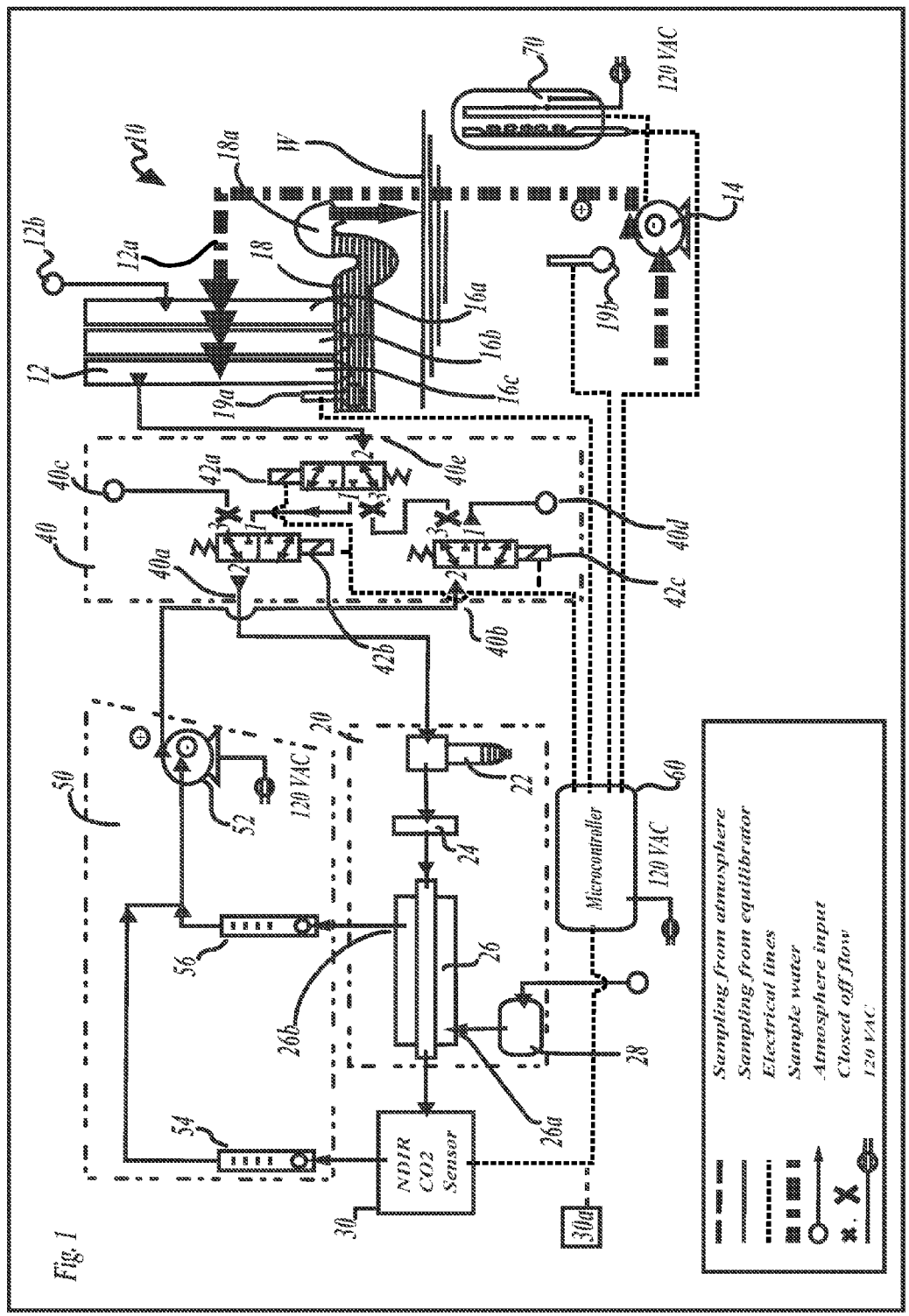
FIG. 1 is a schematic view of a preferred system in a first mode of operation.

Systems and methods are provided for rapid and convenient measurement of dissolved gases in one or more bodies of water. Advantageously, the systems and methods can be used for measuring $pCO_2$ in bodies of water where $pCO_2$ can change rapidly over short time periods and short distances. In particular, the systems and methods can be used to quantify undescribed dynamic patterns of acidification caused by $CO_2$ in coastal ecosystems where rapid changes in $pCO_2$ can be caused by $CO_2$ exchange by riverine input, run-off, coastal flooding, and biological activities such as photosynthesis, respiration including decomposition and other relevant biogeochemical processes. The systems provide automated sampling and measurement of water $pCO_2$ in a device that is small and inexpensive, does not require continuous supervision, and can be deployed on stationary or mobile platforms such as piers or boats.

In brief, the systems are placed in a desired location and take a sample of water at that location and then pass the water through an air:water equilibrator which rapidly brings the a sample of atmospheric air into equilibrium with the $pCO_2$ of water such that the equilibrated air is representative of the water $pCO_2$. The sample air is dried or dehumidified and $pCO_2$ is measured using a simple and portable analyzer, such as an infrared analyzer. The system can sample and measure $pCO_2$ as rapidly as equilibration can occur, or can be programmed to measure $pCO_2$ at predetermined time intervals. To ensure reliability and reproducibility of measurement the system, the system is designed with a sample port 40c that can be configured to automatically sample reference gases to validate proper operation of the system. Validation measures can be made by taking samples of atmospheric air, air that has passed through a portable $CO_2$-stripping filter, such as soda lime, a mixture of calcium hydroxide, sodium hydroxide, potassium hydroxide, and water, or similar acting filter, or a standard gas of known $CO_2$ concentration, any of which can be used to validate the accurate function of the $CO_2$ sensor. Significant deviations from expected $CO_2$ validation measures suggest instrument drift. Although atmospheric $pCO_2$ is not constant, the sustained directional deviations from typical atmospheric concentrations in $pCO_2$, which is currently approximately 400 ppm, can be used to indicate that the sensor requires recalibration or should be replaced. Nearshore $pCO_2$ can range from approximately about 50 ppm to approximately about 30,000 ppm depending on location and season. Pool $pCO_2$ can range from approximately about 50 ppm to approximately 1000 ppm. Measurements can be logged, and measurements can also be broadcast wirelessly or via cellular uplink by the system microcontroller 60 enabling data to be corrected, post facto, based on instrument drift or malfunction. The system can also provide a record of local atmospheric $pCO_2$ when sampling atmospheric air.

Figure 2:
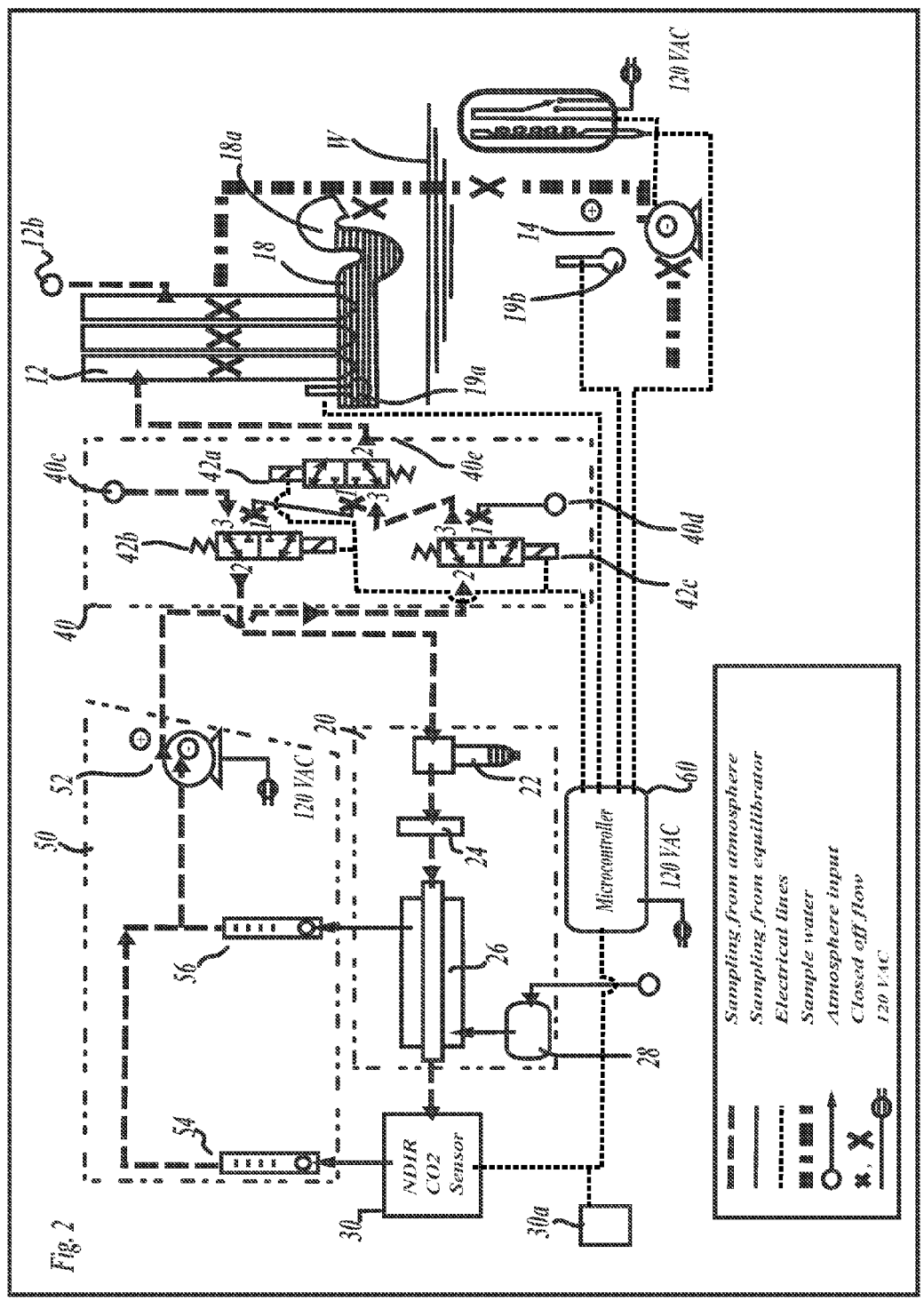
FIG. 2 is a schematic view of the system of FIG. 1 in a second mode of operation.

Shown in FIGS. 1 and 2 is a preferred embodiment of a system or apparatus 10 for determining the concentration of a gas in a fluid sample taken from a liquid source L. The system 10 preferably includes an equilibrator 12 for providing a primary equilibrated gas stream, a drying tube assembly 20 for drying one or more gas streams, a gas analyzer 30 for analyzing the gas stream(s), a control valve assembly 40 that controls the flow of two or more gas streams, including the primary equilibrated gas stream, through the drying tube assembly 20 and analyzer 30; and a gas handling assembly 50 moving the gas streams through the system 10. The components of the system 10 are preferably interconnected by appropriate tubing, such as for example ¼" diameter plastic tubing, for carrying a gas and more preferably an equilibrated gas sample, reference gas, or atmospheric air to be analyzed. The system defines a closed circuit flow path that initiates from a first output port 40*a*. The first output port 40*a* is preferably coupled to the drying tube assembly 20, which is in turn connected to the analyzer 30. The analyzer 30 is preferably coupled to the mover assembly 50; and to close the flow path, the mover assembly 50 is coupled to the first input port 40*b* of the valve assembly 40.

The valve assembly 40 controls or regulates the flow of the various gas streams in and out of the closed flow path of the system 10. The valve assembly 40 can control or regulate automatically. Accordingly, the valve assembly 40 includes a second input port 40*c* for receiving a secondary gas stream, such as for example, atmospheric air or reference gas, and a second output port 40*d* to provide the system 10 with a vent to, for example, atmosphere. The valve assembly 40 preferably couples the equilibrator 12 to the closed circuit of the system 10, preferably by one or more connecting tubes. As previously described, the valve assembly 40 controls the flow of equilibrated gas from the equilibrator 12 to the dry tube assembly 20 and analyzer 30 of the closed circuit. More preferably, the valve assembly 40 includes another port 40*d* and more preferably a two-way port 40*e* to provide for the exchange of gas streams between the closed circuit and the equilibrator in a manner described herein. The valve assembly 40 preferably defines one or more configurations that define the operational modes of the system 10. More specifically, the system preferably includes a detection mode in which the one or more constituent gases of the equilibrated gas stream are detected and analyzed and a cleanout mode in which a gas stream from the positively pressurized port of the vacuum pump 52 is delivered and transported through the system 10 to clean out the system components, such as for example, system tubing, valve ports, and the equilibrator 12. Separate from or alternatively incorporated with the detection and cleanout modes is a validation mode in which the analyzer is assessed and verified to be properly working and which can indicate when it is time to recalibrate or replace the gas detector 30.

Referring again to the schematic drawings of FIG. 1 is a preferred embodiment of the system 10 disposed proximate to a body of liquid and more particularly, water W of which, the concentration of one or more of its constituent gases, i.e., $CO_2$ is to be detected and determined. The water W can be from an estuary source or alternatively from any number of natural or manmade bodies of water. Accordingly, the system 10 of FIG. 1 is shown in a detection mode Water W is delivered to the equilibrator 12 and a first port 12*a* preferably by a submersible pump 14 coupled to the equilibrator by appropriate tubing, such as for example, ⅝" diameter plastic hose. Simultaneously drawn into the equilibrator 12 is atmospheric air through a second port 12*b*. The pump can transport water at a rate of about 10 gallons per hour to about 700 gallons per hour. In one embodiment, the pumping rate is approximately about 100 gallons per hour to approximately about 120 gallons per hour.

The preferred equilibrator 12 is preferably an air-water equilibrator having a series of multiple (e.g., 3) fluidly, e.g. (liquid and gas) connected vertical tubes, 16*a*, 16*b*, 16*c* each having an upper section and a lower section. Other equilibrator configuration designs known in the art can also be used. In one embodiment, each of the vertical tubes 16*a*, 16*b*, 16*c* have their lower sections in fluid communication with drain pipe 18. Generally, water W is carried equally from the submersible pump 14 to the upper sections of all three vertical tubes 16*a*, 16*b*, 16*c* and then drains down the walls of each tube into the common drain pipe 18 and out the drain port 18*a* for return to the body of water W. A preferably continuous stream of air is drawn through the vertical tubes 16*a*, 16*b*, 16*c* so as to commingle with the water sheeting down the insides of each vertical tube in a counter-current direction to the flow of water such that the air stream and one or more of its constituent gases become equilibrated with those of the water W prior to its reaching the drain pipe 18 so as to define the primary equilibrated gas stream prior to entering the valve assembly 40 and gas analyzer 30. More specifically, air is drawn in from the atmosphere into the first tube 16*a* through an inlet port preferably located in the bottom section of the first tube 16*a* and then travels vertically to the upper section of the first tube 16*a* where it is drawn preferably diagonally downward to the bottom section of the second vertical tube 16*b* and subsequently upward vertically to the upper section of the second tube 16*b* where it is pulled or drawn diagonally downward to the bottom section of the third vertical tube 16*c* and subsequently upward vertically to the upper section of the third vertical tube 16*c* and out the port preferably at the upper section of the third tube 16*c* into the valve assembly 40.

The equilibrated gas stream is pulled through the port 40*e* of the preferred valve assembly 40 conveyed out the output port 40*a* and conveyed into the drying tube assembly 20. The drying tube assembly preferably includes a water trap 22, a paper air filter 24, and a drying tube 26. The drying tube 26 is preferably a counter-current drying tube having a central conduit for carrying a gas to be dried, such as for example the equilibrated gas stream or other gas from the gas assembly 40. Preferably surrounding the central conduit is an outer conduit to carry a drying gas stream originating for example from a desiccator 28, which is coupled to an input port 26*a* of the drying tube 26. A preferred drying tube 26 is a dehumidifying Nafion© polymer drying tube. The desiccator 28 draws in atmospheric air or gas from another source to define the drying gas stream. The drying gas stream is drawn or pulled from the exit port 26*b* of the outer conduit of the drying tube 26 such that the drying gas stream flows in a counter current direction to the gas flow in the central conduit of the drying tube 26.

Coupled to the dry tube assembly 20 is one or more gas analyzers 30. The analyzer 30 preferably includes an airtight chamber containing an OEM Non-Dispersive Infrared $CO_2$ sensor, which has preferably been properly calibrated under an appropriate standard, such as for example, nitrogen gas and standardized air mixtures containing known concentrations of $CO_2$. The Non-Dispersive Infrared $CO_2$ sensor and chamber preferably define a compact modular unit that can be plugged, connected or installed within the system in a short manner of time. The time can be less than 1 minute. Analyzer 30, which can be small, easy to install/deinstall, and cost less than ocean going $pCO_2$ monitors, can be easily exchanged with a newly calibrated analyzer 30. A newly calibrated analyzer 30 can be transported to and from a calibration site such as a laboratory, or other regulated location, for controlled calibration procedure. In one embodiment, analyzer 30 can be sized to fit in the front pants pocket of a men's pair of slacks. Newly calibrated analyzer 30 can also be calibrated on site or en route to the site. Preferably integrated with the analyzer 30 and mounted inside the $CO_2$ sensor housing or chamber is a barometric pressure sensor. The barometric pressure sensor can monitor and record deviations in pressure. Pressure monitoring can be used to correct gas concentration measurements because significant deviations from 1 atm will either under or overestimate concentration. Any significant deviations can be in the range from about equal to or greater than about 1% above or below atmospheric pressure. The pressure monitoring can also be used in combination with temperature readings from the temperature probe 19a to correct $pCO_2$ readings when pressure deviates from the expected atmospheric pressure. System 10 can preferably be operated at atmospheric pressure, standard atmospheric pressure is 1013.25 hectopascal (hPa), where deviations from standard atmospheric pressure can be determined by the barometric pressure monitor. In one embodiment, the measured barometric pressure can be used to correct the measured $pCO_2$ based on deviations from standard atmospheric pressure. The dried gas stream flows through the analyzer 30 to determine concentration of constituent gases in the gas stream. More preferably, the analyzer 30 determines or measures the molar concentration of $CO_2$ in the dried gas stream. Where the gas stream being analyzed is the primary equilibrated gas stream, the analyzer 30 determines the molar concentration of the equilibrated gas stream to indirectly determine the concentration of the $CO_2$ of the water W. In addition to measuring the molar concentration of $CO_2$, the analyzer also preferably determines the relative humidity, temperature and barometric pressure of the gas stream being analyzed.

The analyzed gas stream and the drying gas stream are each preferably pulled by the gas handling assembly 50 to be exhausted from the control valve assembly 40. The gas handling assembly 50 preferably includes a vacuum pump having an input coupled to each of the discharge end of the analyzer 30 and the discharge port 26b of the preferred drying tube 26. Accordingly, the gas handling assembly 50 defines the flow rate of the analyzed gas stream and the drying gas stream. More preferably, the flow rates of the gas streams define a differential flow rate. Accordingly, the gas handling system includes a first flow controller 54 to define the flow rate of the analyzed gas stream from the analyzer 30 and a second flow controller 56 to define the flow rate of the drying gas stream. In the first detection mode, the valve assembly 40 is configured for exhaust of the analyzed gas stream from the second exhaust port 40d.

The valve assembly 40 has a second configuration to define the clean out mode of the system 10 as schematically shown in FIG. 2. In the second configuration of the valve assembly 40 atmospheric air, or other reference gas, is drawn into the second input port 40c by the gas handling system 10 for conveyance into the closed circuit of the system 10 and through the dry tube assembly 20 and analyzer 30 for drying and analysis. Other reference gasses can include but are not limited: a gas with a known or a certified $CO_2$ concentration. This reference gas is available commercially and the known or certified $CO_2$ concentration can range from zero to 100%. Other embodiments can include a known or a certified $CO_2$ concentration of 100 ppm, and 400 ppm, 1000 ppm, and 10,000 ppm. Another reference gas can be zero-$CO_2$ concentration gas. One embodiment of a zero-$CO_2$ concentration gas can be an inert gas such as nitrogen. Another reference gas can be $CO_2$-stripped air. One embodiments can include $CO_2$-stripped air produced using a filter that can contains a combination of soda lime and other components that remove $CO_2$ from ambient air. The preferred vacuum pump 52 returns the dried atmospheric gas stream to the valve assembly 40 for discharge from the port 40e to apply a positive pressure to the equilibrator 12 and the tubing coupling the equilibrator 12 to the valve assembly 40. This reversal of gas flow through the equilibrator and its tubing serves to remove any condensation build up generated by high humidity equilibrator air sampling. To further enhance condensation removal, the drying gas stream from the desiccator 28 and the dry tube assembly is also returned to the equilibrator 12 in the second configuration of the valve assembly 40 to facilitate drying along with the atmospheric sample gas stream exhaust. The returning gases are preferably exhausted through port 12b, exiting through 12 and through drain port 18a of the drain pipe 18.

The dried atmospheric gas stream in the closed circuit of the system 10 is analyzed by the analyzer 30 to measure its constituent gases and more preferably the concentration of $CO_2$ of the dried atmospheric air. In a preferred application of the system 10, the atmospheric air has a known relative constant range of $CO_2$ ranging from about 370 ppm to about 430 ppm. Atmospheric air can be used to validate analyzer 30. Global average of $CO_2$ varies within a range of approximately ±30 ppm from the constant. Larger variations in $CO_2$ beyond this range tend to be short-lived, so sustained out-of-range measurements will indicate drift or improper function of analyzer 30. Because the $CO_2$ concentration range is known, the measured value of $CO_2$ in the dried atmospheric gas stream can be compared to the known range to assess the proper functioning of the analyzer 30. In one embodiment, frequent atmospheric measurements can be stored or transmitted and can be used to build data records of local conditions. Local condition records are useful in nearshore settings. In another embodiment, $CO_2$-scrubbed air or standard gases or other references gases via port 40c can provide validation of analyzer 30. Accordingly, the second configuration of the valve assembly 40 and the cleanout mode of the system 10 also preferably provides for an assessment mode to verify the proper operation of the analyzer 30. If the measurement $CO_2$ of the analyzer 30, over a duration of time such as, for example, several hours, is outside the known range, predicted atmospheric variation or known reference gas value by a preferred or user defined percentage, the analyzer 30 can be replaced. More preferably, the analyzer 30 is automatically switched out with an onboard second analyzer 30a or other replacement analyzer 30.

A preferred embodiment of the valve assembly 40 is a set of dual 2-position/3-way solenoid valves 42 for defining each of the first and second configurations of the valve assemblies 40. More preferably, the valve assembly 40 includes a first solenoid 42a coupled to the equilibrator 12 and a second solenoid valve 42b couples the first solenoid valve 42a to the drying tube assembly 20 and provides the inlet port 40c for drawing in the atmospheric air. In another embodiment, other reference gases can be drawn in through inlet port 40c. The valve assembly further preferably includes a third solenoid valve 42c for receiving gas streams returned from the gas handling assembly 50 and controlling the flow of return gas to either the exhaust port 40d in the first configuration of the valve assembly 40 or diverting the dried gas to the first solenoid valve 42a to clean out the equilibrator 30 and remove condensation from sample tubes connecting 12 to 40e. In one preferred embodiment of detection mode of the system 10 the solenoid valves, 42a, 42b, and 42c are de-energized, a vacuum generated by the vacuum pump 52 pulls sample gas from the equilibrator 12 through open ports in the solenoid valve system 42, passes through the entire system and is ultimately vented back to the atmosphere via the vacuum pump 52 to the discharge port 40d of the third solenoid valve 42c, as seen in FIG. 1. When the solenoid valves 42a, 42b, and 42c are preferably energized in the second configuration of the valve assembly 40, sample collection is diverted from the equilibrator 12 by the second solenoid valve 42b to the open atmospheric sample port 40c in order to take $CO_2$ measurements of the atmosphere. In another embodiment, a reference gas is sampled through port 40c. At the same time, positive pressure exhaust from the vacuum pump 50 is directed through the third and first solenoid valves 42c, 42a to reverse the air flow between the first solenoid valve 42a and the equilibrator 12 for exhaust from the equilibrator port 12b, as indicated by a dashed arrow between the two in FIG. 2; or alternatively or in addition to exhausting from the exit port 18a of the drain pipe 18.

The system 10 preferably includes a controller 60 that includes custom configuration and programming that controls the operation and data acquisition of the instrument. In one preferred embodiment of the system 10, the controller 60 is a programmable microcontroller 60 which provides voltage signals to energize and de-energize the valve assembly 40 at programmed frequencies and for durations to define the first and second configurations of the assembly 40 and the operation modes of the system 10. For example, the microcontroller 60 maintains the valve assembly 40 de-energized in the first configuration for a duration of, for example, 48-50 minutes of one hour to maintain the system in the detection mode of the water body's $pCO_2$ during the duration. The microcontroller 60 then energizes the valve assembly 40 to define the second configuration for 10-12 minutes, for example, of the hour to maintain the system in the cleanout and preferred assessment mode of the system 10. In this mode, either atmospheric gas or reference gas measurements can be made. In an embodiment, valve assembly 40 is in the first configuration for 24-36 minutes of every hours and in the second configuration for 24-36 minutes of every hour where the controller cycles valve assembly 40 between the first configuration and the second configuration three times an hour. Other frequencies and durations are possible for each of the operating modes provided the programmed frequencies are sufficient to measure the fluid samples and maintain system operation over an extended period without operator intervention. In order to energize the valve assembly 40, the microcontroller 60 is preferably coupled to a power source 70 (FIG. 1) of the system 10. The power source 70 is preferably a 120 volt A/C power supply or may alternatively be a DC power supply, solar power/batteries, portable generator and power inverter. The power source 70 preferably also powers the submersible pump and the preferred vacuum pump 52. Alternatively, the components can be independently powered by independent power sources.

The system 10 can operate on a 120 volt AC standard electrical line, a portable electricity generator including gasoline and diesel generators, battery with power inverter including for example a bank of 12 volt batteries, photovoltaic solar panels, or any number of other sources of electrical power including, but not limited to, for example, wind generators and hydroelectric power. In an embodiment, system 10 can be programmed to operate intermittently or on a less frequent but desired duty cycle to save power. The intermittent duty cycles can range from continual once per minute measurements and data logging to low frequency recording including measurements record once every hour or longer interval if desired. Other intermittent duty cycles include 2 measurements per hour, 3 measurements per hour, 4 measurements per hour, 5 measurements per hour, 6 measurements per hour, 7 measurements per hour, 8 measurements per hour, 9 measurements per hour, 9 measurements per hour, and 10 measurements per hour, up to 60 per hour. The intermittent duty cycles can also operate more frequently and the intermittent duty cycles can include 1 measurement per minute, 2 measurements per minute, 3 measurements per minute, 4 measurements per minute, 5 measurements per minute, 6 measurements per minute, 7 measurements per minute, 8 measurements per minute, 9 measurements per minute, and 10 measurements per minute.

In embodiments, system 10 can be powered by an external source having its own ground-fault interrupter. In other embodiments, system 10 can include the ground-fault interrupter as one of its components when that component is not a part the power source. For any monitoring application, two or more of the system 10 can be deployed. In certain embodiments each of the two or more of the system 10 have their own power source. In other embodiments, the power source is shared between all of the two or more of the system 10. In another embodiment, a first and a second equilibrator 12 can be provided, and submersible pumps 14 can be powered and controlled via controller 60, the second equilibrator 12 can be ported to port 40c. The second equilibrator 12 can substitute for an atmospheric or reference gas.

In addition to controlling the configuration of the valve assembly 40, the microcontroller 60 preferably controls operation of other components of the system 10, records measured parameters, and/or communicates with other onboard and remote system equipment. For example, the microcontroller preferably powers the analyzer 30 and programs the frequency and duration of its measurements. The microcontroller 60 preferably appropriately logs the $CO_2$ concentration of the various gas streams passing through the analyzer 30. In addition, the microcontroller 60 preferably monitors and records the temperature, pressure, relative humidity and global position of the analyzer 30 and its chamber by collecting data from a barometric pressure module integrated with the analyzer 30 and a global positioning system (GPS) module preferably integrated with the microcontroller 60.

The microcontroller is also preferably coupled in communication with the submersible pump 14 to turn on the pump in detection operating mode of the system 10 (FIG. 1) and turning off the pump in the cleanout mode (FIG. 2). Moreover, it is desirable to know the liquid temperatures in both the body of the water W being tested and the collected sample maintained in the equilibrator 12. Accordingly, the system preferably includes a first liquid temperature probe 19a disposed in contact with the fluid in the equilibrator 12 and a second liquid probe 19b disposed in the body of water W. The microcontroller preferably monitors and records the temperature measurements from each of the first and second temperature probes 19a, 19b.

The microcontroller 60 includes appropriate on-board memory to record and store its collected data. All data are preferably stored in a .csv file on a flash memory card; however, other file types and storage techniques are possible. The microcontroller 60 can be integrated or interface with an on-board appropriate user display, such as for example, a digital display to provide real time readout of $CO_2$, temperature or other recorded data. Alternatively or in addition to, the microcontroller 60 can communicate wired or wirelessly with remote equipment on site or remotely located around the world. Remote equipment can include but is not limited to a computer, an internet access point, a tablet, and a cellular phone. Accordingly, the microcontroller is equipped with appropriate communication interface equipment and software, including for example, USB, wired, wireless, radio cellular, Wi-Fi, blue-tooth and/or smartphone ports, cards and/or drivers, apps and other related technology.

System 10 is capable of storing and transmitting the measured $CO_2$ data. The device is also capable of storing and transmitting the ancillary data collected alongside of the $CO_2$ data. The ancillary data can include temperature, barometric pressure, relative humidity, voltage measurements, error codes, and location data. All these data, the $CO_2$ data and the ancillary data can be stored on a permanent or removable digital media including hard drives, compact flash (CF), secure digital memory (SD), flash or thumb drives, or any other media known in the art. The data can also be transmitted to a second location including to computers, cellular telephones, tablets, or any other device capable of receiving transmitted data. In an embodiment, the device capable of receiving transmitted data has an application for receiving the data from system 10. The data can be pushed to the second location or the second location can pull the data from the system 10. The data can be pushed or pulled to a website on the internet. In an embodiment, a smartphone application can receive pushed data at preset intervals from system 10. In another embodiment, the smartphone pulls the collected data from system 10. In another embodiment, a computer application can pull the data collected form system 10 into a desktop or laptop application. In further embodiments, the data can be transmitted through a wired component such as Ethernet, USB, firewire, coaxial cable, telephone landlines and any other wired transmission component known in the art. In other embodiments, the data can be transmitted through a wireless component such as Wi-Fi, Bluetooth, cellular telephone networks including, but not limited to, a global system for mobile communications (GSM), code division multiple access (CDMA), personal communications service (PCS), and any other wireless network known in the art. In one embodiment, the data is stored on a removable SD having a Wi-Fi transmitter that can transmit, for example, $CO_2$ and ancillary data from system 10 to a tablet for manipulation and analysis.

Figure 3:
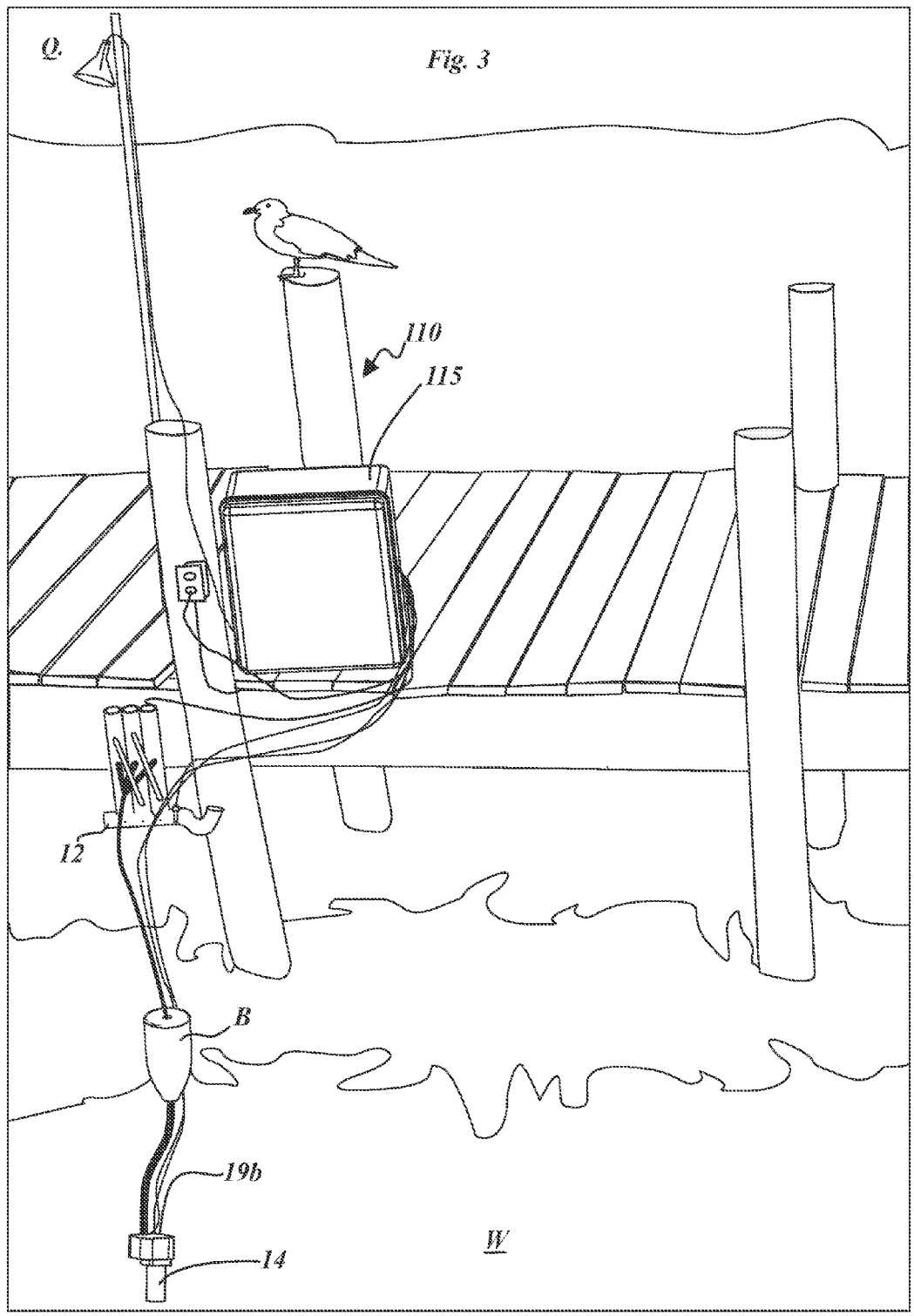
FIG. 3 is a preferred embodiment of the system of FIG. 1 deployed proximate a body of water to be analyzed.

The system 10 is preferably portable for deployment to the site of the water body W to be analyzed. A preferred embodiment of the system 110 is shown in FIG. 3 and FIG. 4, in which the system 110 is substantially enclosed in a housing 115. The housing is preferably a water resistant housing 115 having a base 115a in which system components are disposed and a cover 115b to enclose the system 110. A preferred housing 115 preferably measures about 60-65 cm.× about 50 cm× about 30 cm. Accordingly, the system 110 and its enclosure are preferably sized for handling by a single operator to be deployed to a site proximate the water body W to be analyzed. Once the preferred system 110 is deployed, the submersible pump 14 and second temperature probe 19b is disposed in the water W, where it may be suspended from buoy B, and the preferred air-water equilibrator is mounted external of the system housing 115 and above the water W. The housing is disposed out of but in close proximity to the water and coupled to a power supply 70. Where for example, the system 110 is deployed in an estuary, the system 110 and its housing can be disposed along a dock as seen, for example, in FIG. 3. Because the system 110 is generally exposed to the outdoor elements including sun, water, rain or other precipitation, the housing 115 preferably provides a substantially water resistant housing to protect the internal components of the system 110. Moreover, system 110 provides for sufficient cooling to maintain the internal temperatures of the housing 115 within the appropriate operating temperatures of the internal components.

Shown in FIG. 4 is an exploded view of the preferred system 110. The base 115a engages the cover 115b to preferably define a fluid tight seal there between. The housing 115 and more preferably its base 115a can include one or more perforations or openings to allow for wired or cabled connections between the internal components of the system 110 and external equipment. More specifically, the base 115a can include one or more openings with an appropriate water proof/water resistant fitting or connector affixed in the opening using a plastic weld or other appropriate sealing technique. For example, a water resistant fitting can be disposed about the box to provide a cable connection to the internal microcontroller 60.

In the preferred embodiment of the system 110 shown in FIG. 4, the housing 115 is constructed to provide desired cooling and/or water resistance. Disposed within the housing 115 is the preferred vacuum pump 52 of the gas handling system 50 previously described. The vacuum pump 52 preferably includes a cooling fan. In the preferred embodiment of the system 110, the cooling fan of the vacuum pump is used to cool or maintain the internal temperature of the housing 115. More specifically, the vacuum pump 52 and its fan are preferably disposed within the base 115a of the housing such that the cooling fan can draw in ambient air through the housing to cool and maintain the internal space of the housing within appropriate operating temperatures. The housing 115 preferably includes an appropriate vent to allow the cooling air to escape and carry away the heat generated from the internal components or the radiant heat generated by external heat sources, such as, for example, sun light.

Preferably disposed about the vacuum pump 52 and its cooling fan is a shield 53. The base 115a preferably includes an opening or aperture that is sized to allow for the shield 53 and its flange to be mounted and secured to the base 115a. The shield 53 preferably includes an aperture 55 disposed proximate the cooling fan of the pump 52 through which ambient air can be exhausted for cooling the housing 115a.

Preferably disposed about the housing 115 is an intake vent 57. The vent 57 is located such that it permits the cooling fan to draw in cooling ambient air to flow across the system components and draw away the generated heat. Moreover the vent 57 is preferably configured to keep water out of the internal chamber of the housing 115 and the system electronic components. In one particular embodiment, the vent 57 is configured as an elbow, "snorkel" or other structure having a bend. The bend is preferably located along the vent 57 such that the internal configuration of the bend prevents any significant amount of water or moisture collected on the outside of the housing 115 from traveling into the internal space and damaging the internal components of the system 110.

Shield 53 can include an electrical receptacle. In one embodiment, water pump 14 is powered via a communication to the electrical receptacle. In another embodiment, an electrical receptacle can provide power to system 110 and can be coupled to power source 70. External power sources can include 120 volt A/C power supply or may alternatively be a DC power supply, solar power/batteries, portable generator and power inverter. Shield 53 can contain one more pass-through ports. Temperature sensor cables 19a and 19b can traverse the pass-through port of shield 53 and can be coupled to control unit 60. In one embodiment, a pass-through port contains a bulkhead fitting connection for an internal temperature sensor cable to communicate with an external temperature sensor cable. In another embodiment, equilibrator 12 can be coupled to port 40e via a pass-through port. In yet another embodiment, port 40c can be coupled to atmospheric air sampling shroud Q via a pass-through port. In an embodiment, a pass-through port is configured with a bulkhead union with push on quick release fittings. In this configuration, the tubing coupling between port 40e and equilibrator 12 has more than one tube, an external tubing coupling and an internal tubing coupling. In another configuration, the tubing coupling between port 40c and atmospheric air sampling shroud Q has more than one tube, an external tubing coupling and an internal tubing coupling. In one embodiment, an external master power switch that can be configured to turn on and off power to select or all electrical components in and outside of system 110, is mounted on shield 53. In another embodiment, shield 53 contains a weather resistant shroud. In one embodiment, the weather resistant shroud can be configured to prevent water from entering housing 115 and for passage of exhaust air and electrical, temperature, and air tube connections.

System 110, preferably configured as a $pCO_2$ monitoring system, can be deployed in near shore ecosystems. Near shore ecosystems refer to bodies of water having some salt in them, either fully marine, bodies of water that are brackish, or bodies of having substantially fresh water. Brackish water results from the mixing of fresh water and salt water, such as occurs in an estuary. Some examples of near shore bodies of water include, coastal ocean, bays and harbors, estuaries (like the Chesapeake Bay where tidal ocean waters meet fresh water riverine inputs), coastal lagoons, fjords, freshwater lakes and rivers. Near shore ecosystems, such as for example, freshwater, waste water or drinking treatment plants can also include engineered or man-made bodies of water including ponds, reservoirs, aquaculture facilities (indoor facilities as well as monitoring of outdoor environments where animals such as shellfish are out-planted), wastewater treatment plants, drinking water treatment plants, and private and municipal swimming pools. Embodiments include devices that measure $pCO_2$ in these ecosystems. Other examples of a near shore ecosystem are fringing habitats such as tidal saltmarshes and mangrove forests. In these areas, trees and other plants grow in tidal waters, partly submerged in tidal salt water, that are alternately inundated and drained at high and low tides, that enable plants and the biogeochemical processes associated with the soils they are growing in to influence water chemistry. In an embodiment, the $pCO_2$ monitoring system measures $pCO_2$ in this near shore or similar ecosystem. Another example of a near shore ecosystem includes seagrass meadows, which grow underwater in intertidal and subtidal habitats. In an embodiment, the $pCO_2$ monitoring system measures $pCO_2$ in this near shore ecosystem.

The system 110, preferable configured as a $pCO_2$ monitoring system, can be deployed singly or multiply as part of a network of monitoring devices. The system 110 can be deployed in a stationary configuration, a mobile configuration or in a combination of stationary and mobile systems. In the stationary configuration, $pCO_2$ is measured at a fixed location. Some examples of a stationary configuration include placement on land include piers and docks. Examples of a stationary configuration at sea include floating and fixed platforms. In the mobile configuration, $pCO_2$ is measured across multiple locations. Examples of mobile deployments include boats of various sizes ranging from small skiffs to large research vessels. Stationary and mobile configurations can be deployed in the same system. The stationary systems measure $pCO_2$ from fixed locations while the mobile $pCO_2$ monitoring systems measure $pCO_2$ from mobile locations which can be across space, for example along a transect where the monitoring system can be configured to detect $pCO_2$ spatial gradients and variation. The scalability of increasing numbers of stationary $pCO_2$ monitoring systems increases spatial resolution and deploying mobile $pCO_2$ monitoring systems in tandem with the stationary $pCO_2$ monitoring systems can further increase the spatial resolution by filling in the gaps among the stationary $pCO_2$ monitoring systems.

The $pCO_2$ monitoring system can be co-located with existing water quality monitoring stations. A system deploying $pCO_2$ monitoring systems and existing water quality monitoring stations can take advantage of existing geographic coverage and complementary water quality measurements such as salinity, specific conductivity, wind direction and speed, chlorophyll content, turbidity, light level, water depth, dissolved oxygen, pH. Furthermore, co-location provides measurement ground-truthing of shared measurements such as, for example, water temperature.

In embodiments described herein, the $pCO_2$ monitoring system can be deployed in a near shore ecosystem that includes private and municipal swimming pools. In one embodiment, pH control can be employed to optimize the efficacy of disinfection agents. The system deployed in pools can include a pH regulator and in embodiments the pH regulator is a $pCO_2$ monitoring system that can be combined with a $CO_2$ injection system. The $CO_2$ injection system can be used to lower the pH. In another embodiment, a disinfectant dispenser can be combined with the $pCO_2$ monitoring system and can be combined with the $CO_2$ injection system. In an embodiment, the disinfectant is chlorine. In an embodiment of the pool $pCO_2$ monitoring system, the $pCO_2$ monitoring system measures $CO_2$ in the swimming pool, transmits a signal to the pH regulator, and the pH regulator adjusts the pH of the pool. The signal sent is a value that is transmitted to a microcontroller, such as a computer, that calculates pH. In one embodiment, pH is determined from the $pCO_2$ and a total alkalinity measure, which is the buffering capacity of the pool water. The total alkalinity can be measured independently. Total Alkalinity is substantially constant compared to $pCO_2$ and pH such that for any given total alkalinity, $pCO_2$ corresponds to a specific pH value or narrow range of pH values. In an embodiment, the pH regulator can adjust the pool pH by releasing a pH regulating substance. A preferred substance to regulate pH is $CO_2$. The pool $pCO_2$ monitoring system can also have a feedback loop where the $pCO_2$ monitoring system measures $pCO_2$ more than once in conjunction with the pH regulator to adjust the pool's pH. The $pCO_2$ monitoring system provides feedback signals to the pH regulator to release more or stop releasing substances that regulate pH based on the multiple measurements of pool $pCO_2$. In one embodiment, the $CO_2$ injector automatically delivers $CO_2$ to reduce pH or shuts off the flow of $CO_2$ and allows pH to rise passively as $CO_2$ off-gasses from the pool. The pH regulator can automatically maintain pH within an optimized range. For example, one optimized range is approximately about 7.2-7.8. Use of $CO_2$ for adjusting pH to an optimized pH range, can limit the need for use and storage of dangerous acids such as hydrochloric acid, which when accidentally mixed with certain disinfectants can produce deadly gas and caustic bases such as sodium carbonate. Use of $CO_2$ as a pH control agent can decrease the amount of disinfectant chlorine required, minimizing eye irritation and the production of above-water oxidants and in-water trihalomethanes.

Another embodiment is a continuous $pCO_2$ monitoring system configured for use in conjunction with a micro algae carbon capture system that is configured to biologically sequester $CO_2$ from, for example, industrial plants and fossil fuel power plants, to prevent the $CO_2$'s release into the atmosphere. In one embodiment, $pCO_2$ monitoring system can measure $CO_2$ before and after micro algae carbon capture systems sequester $CO_2$. In another embodiment, the continuous $pCO_2$ monitoring system can be located in or around a commercial shellfish or finfish hatcheries, and around microalgae culturing facilities. The $pCO_2$ monitoring system can measure $CO_2$ values. Data from the $pCO_2$ monitoring system can also be combined with measurements such as total alkalinity or total inorganic carbon to calculate other carbonate parameters such as carbonate, bicarbonate, calcium carbonate saturation state, and pH. All measures can be stored and/or transmitted.

The design and operation of system 110 allow it to operate unattended for extended periods of time. The time can range from at least about 1 day to at least about 1 month to at least about one year or longer. In certain configurations, operation of system 110 can be optimized by periodic cleaning and maintenance measures. For example, the ability to alter the duty cycle of data collection and transmission, and the water and weather resistant qualities of system 110 allow for the system to be deployed and allowed to collect data without the need for continuous maintenance. In certain embodiments, the system 110 can be left unattended for between at least about 1 month and at least about 1 year. In other embodiments, the system 110 can be left unattended for between at least about 1 month and at least about 6 months. In still other embodiments, the system 110 can be left unattended for between at least about 1 and at least about 3 months. In still other embodiments, the system 110 can be left unattended for at least about 1 month. In yet another embodiment, the system 110 can be left unattended between at least about 1 day and at least about 1 year. In another embodiment, the system 110 can be left unattended between at least about 1 day and at least about 1 month.

While the present systems and methods have been disclosed with reference to certain embodiments, numerous modifications, alterations, and changes to the described embodiments are possible without departing from the sphere and scope of the present invention, as defined in the appended claims. Accordingly, it is intended that the systems and methods are not limited to the described embodiments, but have the full scope defined by the language of the following claims, and equivalents thereof.

What we claim is:

1. An apparatus for measuring the partial pressure of $CO_2$ in a water body, the apparatus comprising:
   an air-water equilibrator providing an equilibrated gas sample equilibrated from water of the water body;
   a drying tube assembly;
   a gas analyzer;
   a control valve assembly, including a first control valve, a second control valve and a third control valve, each of the first and second control valves having a first input port, a second input port and an output port, the third control valve having an input port, a first output port and a second output port, the first input port of the first control valve being coupled to the equilibrator, the output port of the first control valve being coupled to the first input port of the second control valve, air or a reference gas source being coupled to the second input port of the second control valve, the output port of the second control valve being coupled to the drying tube assembly, the input port of the third control valve being coupled to the gas analyzer, the first output port of the third control valve defining an exhaust port, and the second output port of the third control valve being coupled to the second input port of the first control valve; the control valve assembly having a first configuration for coupling the equilibrator and the drying tube assembly and a second configuration for coupling the source of air or the reference gases and the drying tube assembly; and
   a controller coupled to the control valve assembly to control the control valve assembly between the first and second configuration;
   wherein the gas analyzer is coupled to the drying tube assembly for taking a $CO_2$ measurement of the equilibrated gas sample when the control valve assembly is in the first configuration and taking a $CO_2$ measurement of the air or reference gas, when the control valve assembly is in the second configuration.

2. The apparatus of claim 1, further comprising a pump wherein in the first configuration of the control valve assembly, the pump circulates the equilibrated gas from the equilibrator to the control valve assembly through the drying tube assembly and the gas analyzer and wherein the equilibrated gas is exhausted from the control valve assembly.

3. The apparatus of claim 1, further comprising a pump wherein, in the second configuration of the valve assembly, the pump circulates the air or reference gas from the control valve assembly through the drying tube assembly and the gas analyzer and wherein the air or reference gas is exhausted from the equilibrator, the $CO_2$ measurement of the air or reference gas being used to assess the gas analyzer.

4. The apparatus of claim 1, wherein the drying tube assembly includes a coaxial drying tube for moving a drying gas counter-current to at least one of the equilibrated gas and the air or reference gas.

5. The apparatus of claim 4, further comprising a pump which pulls the drying gas and at least one of the equilibrated gas and the air or reference gas in a counter-current direction to one another.

6. The apparatus of claim 4, wherein the air or reference gas and the drying gas define a differential flow rate.

7. The apparatus of claim 1, further comprising a submersible pump coupled to the equilibrator to supply water from the water body.

8. The apparatus of claim 1, further comprising a first temperature probe to measure water temperature in the equilibrator and a second temperature probe to measure water temperature in the water body, the first and second temperature probes being coupled to the controller.

9. The apparatus of claim 1, wherein the controller alters the control valve assembly between the first and second configurations at a predetermined frequency.

10. The apparatus of claim 9, wherein the predetermined frequency is one time per hour.

11. The apparatus of claim 9, wherein the predetermined frequency is 3 times per hour.

12. The apparatus of claim 9, wherein the controller places the control valve assembly in the first configuration for a duration of 48-50 minutes of every hour and in the second configuration for a duration of 10-12 minutes for every hour.

13. The apparatus of claim 9, wherein the controller places the control valve assembly in the first configuration for a duration of 24-36 minutes of every hour and in the second configuration for a duration of 24-36 minutes for every hour, and wherein the controller cycles through the first and second configurations three times every hour.

14. The apparatus of claim 1, wherein the apparatus is portable comprising a housing and a pump, and further comprising a cooling fan for cooling said pump and said housing, wherein said housing includes an intake vent having a bend to prevent water from entering said housing.

15. A system for measuring $CO_2$ in one or more locations comprising one or more portable $CO_2$ monitoring devices, each comprising an apparatus according to claim 14, the one or more portable $CO_2$ monitoring devices being located in a near shore ecosystem.

16. The system of claim 15, wherein the near shore ecosystem is selected from the group consisting of a private and a municipal swimming pool.

17. A method for determining changes in $CO_2$ concentration in a body of water over a period of time employing an apparatus according to claim 1 comprising:
(a) equilibrating a water sample taken from said body of water at a first time point with a sample of air such that a concentration of $CO_2$ in the equilibrated air is representative of a concentration of $CO_2$ in said water sample prior to equilibration;
(b) drying the equilibrated air;
(c) measuring the concentration of $CO_2$ in said equilibrated air with a $CO_2$ sensor and calculating the concentration of $CO_2$ in said water sample,
(d) repeating steps (a)-(c) for one or more subsequent time points, and
(e) for each time point where a concentration of $CO_2$ in a sample of dried air was measured, comparing said measured concentration with a standard measurement, thereby assessing the reliability and accuracy of the measurements obtained in steps (c).

18. The method of claim 17 wherein the equilibrating step comprises:
transporting water continuously through a tube from a submerged water pump to an air-water equilibrator.

19. The method of claim 17 wherein said drying step comprises: transporting the equilibrated air through a water trap, a paper filter, and a counter-current drying tube to dry the equilibrated air prior to the equilibrated air reaching the $CO_2$ sensor and thereby preventing particulates or liquid from contacting the $CO_2$ sensor.

20. An apparatus for measuring the partial pressure of $CO_2$ in a water body, the apparatus comprising:
an air-water equilibrator providing an equilibrated gas sample equilibrated from water of the water body;
a drying tube assembly;
a control valve assembly having a first configuration for coupling the equilibrator and the drying tube assembly and a second configuration for coupling a source of atmospheric air or other reference gases and the drying tube assembly;
a controller coupled to the control valve assembly to control the control valve assembly between the first and second configurations;
a gas analyzer coupled to the drying tube assembly for taking a $CO_2$ measurement of the equilibrated gas sample when the control valve assembly is in the first configuration and taking a $CO_2$ measurement of an air or a reference gas, when the control valve assembly is in the second configuration; and
a pump wherein, in the second configuration of the valve assembly, the pump circulates the air or reference gas from the control valve assembly through the drying tube assembly and the gas analyzer and wherein the air or reference gas is exhausted from the equilibrator, the $CO_2$ measurement of the air or reference gas being used to assess the gas analyzer.

* * * * *